United States Patent
Kinoshiro et al.

(10) Patent No.: US 9,068,237 B2
(45) Date of Patent: Jun. 30, 2015

(54) METHOD FOR DESULFURIZING HOT METAL

(75) Inventors: Satoshi Kinoshiro, Kawasaki (JP); Kyoko Fujimoto, Chiba (JP); Masao Inose, Chiba (JP); Toshiyuki Ito, Kawasaki (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 14/119,692

(22) PCT Filed: Aug. 8, 2012

(86) PCT No.: PCT/JP2012/070202
§ 371 (c)(1),
(2), (4) Date: Nov. 22, 2013

(87) PCT Pub. No.: WO2013/024765
PCT Pub. Date: Feb. 21, 2013

(65) Prior Publication Data
US 2014/0083251 A1     Mar. 27, 2014

(30) Foreign Application Priority Data

Aug. 12, 2011 (JP) .................. 2011-176634

(51) Int. Cl.
*C21C 1/02* (2006.01)
*G01N 21/64* (2006.01)
(Continued)

(52) U.S. Cl.
CPC *C21C 1/02* (2013.01); *G01N 21/64* (2013.01); *G01N 21/643* (2013.01); *G01N 2021/6432* (2013.01); *C21C 7/064* (2013.01); *G01N 33/203* (2013.01)

(58) Field of Classification Search
CPC ............ C21C 1/02; G01N 21/64; G01N 1/44; G01N 21/643; G01J 3/4406
USPC .................. 75/10.12, 10.14, 10.15, 384, 377
See application file for complete search history.

(56) References Cited

U.S. PATENT DOCUMENTS

| 4,360,381 | A | * | 11/1982 | Tarutani et al. ................. 420/42 |
| 4,944,798 | A | * | 7/1990 | Ototani ........................... 420/85 |
| 5,149,364 | A | * | 9/1992 | Craig et al. ..................... 75/566 |

FOREIGN PATENT DOCUMENTS

| JP | A-54-139819 | 10/1979 | |
| JP | 61191956 A | * 8/1986 | ............. G01N 27/44 |

(Continued)

OTHER PUBLICATIONS

Gyun et al. Patent publication KR 20050007494 A published Jan. 19, 2005. Abstract.*

(Continued)

*Primary Examiner* — George Wyszomierski
*Assistant Examiner* — Tima M McGuthry Banks
(74) *Attorney, Agent, or Firm* — Oliff PLC

(57) ABSTRACT

In a method for desulfurizing hot metal by analyzing S concentration of a sample taken out from the hot metal, the S concentration is analyzed rapidly and precisely by a method comprising a high frequency induction heating step of oxidizing the sample under a high frequency induction heating in a pure oxygen atmosphere to convert S in the hot metal to $SO_2$ and an analysis step of analyzing $SO_2$-containing gas generated in the high frequency induction heating step through an ultraviolet fluorescence method to quantify S concentration in the sample, whereby S concentration after the desulfurization is controlled precisely and hence fault of S concentration is prevented but also the increase of the cost due to the excessive addition of a desulfurization agent and step disruption at steel-making step are prevented.

4 Claims, 1 Drawing Sheet

(51) Int. Cl.
*C21C 7/064* (2006.01)
*G01N 33/20* (2006.01)

(56) References Cited

FOREIGN PATENT DOCUMENTS

| JP | A-8-94609 | 4/1996 | | |
|---|---|---|---|---|
| JP | A-2000-065699 | 3/2000 | | |
| JP | A-2001-323314 | 11/2001 | | |
| JP | A-2002-241823 | 8/2002 | | |
| JP | 2004138466 A | * 5/2004 | ............ | G01N 21/64 |
| JP | A-2004-138466 | 5/2004 | | |
| JP | A-2005-290434 | 10/2005 | | |
| JP | A-2006-199981 | 8/2006 | | |
| JP | A-2006-322863 | 11/2006 | | |
| JP | A-2009-144221 | 7/2009 | | |
| JP | A-2009-191300 | 8/2009 | | |
| JP | A-2010-163697 | 7/2010 | | |
| JP | A-2011-237204 | 11/2011 | | |

OTHER PUBLICATIONS

Machine translation of KR 20050007494 A published Jan. 19, 2005.*
Jun. 19, 2014 Office Action issued in Chinese Patent Application No. 201280024714.5 (with statement of relevance).
Sep. 23, 2014 European Search Report issued in International Patent Application No. PCT/JP2012/070202.
"As to desulfurization method using agitation blade," *Tetsu-to-Hagane*, 1972, vol. 58, No. 4, p. 34 (with partial translation).
Kurokawa et al., "The Development in Hot Metal Desulphurization Process," *Sumitomo Metal Technical Reports*, 1993, vol. 45, No. 3, pp. 52-58 (with abstract).
"As to desulfurization of hot metal by means of quicklime," *Tetsu-to-Hagane*, 1978, vol. 64, No. 2, pp. A21-A24 (with partial translation).
International Search Report issued in International Patent Application No. PCT/JP2012/070202 mailed Sep. 11, 2012.

* cited by examiner

METHOD FOR DESULFURIZING HOT METAL

TECHNICAL FIELD

This invention relates to a desulfurization method of hot metal, and more particularly to a method for desulfurizing hot metal wherein S concentration in the hot metal can be controlled in a high accuracy by analyzing S concentration in the hot metal rapidly and accurately.

RELATED ART

Recently, it is increasingly demanded to make the quality of iron and steel products higher, and it is an important subject to reduce S contained in steel associated therewith. Since most of S contained in the steel product results from iron ore or coke, a great amount of S is included in hot metal tapped from a blast furnace. At steps after the tapping from the blast furnace is carried out desulfurization for reducing S in the hot metal or in molten steel.

Typically, a process for conducting the desulfurization is roughly divided into a hot metal pretreating process and a secondary refining process. In general, the hot metal pretreating process and the secondary refining process are co-used in case of a low-sulfur steel having S concentration contained in final product of not more than 0.003 mass % or an extremely low-sulfur steel having S concentration of not more than 0.001 mass %, while desulfurization is frequently carried out only by the hot metal pretreating process in case of plain steels having S concentration of more than 0.003 mass %.

In the desulfurization by the hot metal pretreating process is widely used a desulfurization agent composed mainly of lime (CaO). In this case, the desulfurization reaction proceeds based on the following reaction formula:

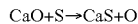

As mentioned above, the steels other than the low-sulfur steel or extremely low-sulfur steel are desulfurized only by the hot metal pretreating process without conducting desulfurization in the secondary refining. Because of this, the desulfurization treatment in the hot metal pretreating process becomes important.

As a desulfurization method by the hot metal pretreating process is known a method using a mechanical agitation type desulfurization apparatus (which may be said as "KR" hereinafter) (see, for example, Patent Documents 1~3 and Non-patent Documents 1~3). In general, the hot metal tapped from the blast furnace is transferred to steel-making steps with a torpedo car, a hot metal ladle or the like and then charged into a converter with a charging ladle as an exclusive ladle. However, the desulfurization treatment by the above KR is commonly carried out by inserting cross-shaped blades (impeller) made from a refractory into the hot metal ladle or the charging ladle and adding the desulfurization agent from above while rotating the central part of the ladle at a high speed.

In the desulfurization treatment using KR, the desulfurization agent is dispersed in the hot metal by rotating the impeller immersed in the hot metal to progress the desulfurization reaction. Therefore, the desulfurization is carried out by continuing agitation for a given time after the addition of the desulfurization agent, taking out the impeller through the stop of the rotation after the completion of the desulfurization reaction, and then removing desulfurized slag with a high S concentration floated on the hot metal by means of a slag dragger or the like. The hot metal after the desulfurization is then charged into the converter and refined into steel.

The conditions in the desulfurization treatment using KR such as rotating speed, rotation number and immersion depth of the impeller, addition amount of desulfurization agent and so on are determined from concentration of S contained in hot metal before desulfurization, target S concentration after desulfurization (standard value of S), kind of desulfurization agent, amount of hot metal and so on. However, the impeller used in the KR is made from the refractory, so that it is worn with the increase of use number. In addition, the worn shape of the impeller is not constant and is irregular. To this end, the agitation force decreases or varies with the increase of the use number even under the same agitation condition, which causes variation in the desulfurization effect. Also, the desulfurization effect is changed even by varying particle size of the desulfurization agent, temperature of hot metal and the like. Therefore, desulfurization up to the target S concentration may not be attained in some situations.

When the desulfurization is carried out only by the hot metal pretreating process, the fault of S concentration after the desulfurization requires re-desulfurization treatment. The analysis result of S concentration after the desulfurization is identified around the time of the transfer of the hot metal ladle or the like to a converter yard, so that when the fault of S concentration is identified, it is necessary to again return the hot metal ladle or the like to the hot metal pretreating installation. As such a situation is caused, the start of blowing in the converter is largely delayed or the interruption of continuous casting or the like is caused, whereby step disruption is involved. In the desulfurization treatment of the hot metal, therefore, an excessive amount of the desulfurization agent is charged for avoiding the above situation to avoid the fault of S concentration, which brings about the increase of the production cost.

The S concentration in hot metal is obtained by analyzing a pig iron sample taken and solidified from the hot metal. As a method of analyzing S concentration in hot metal are mainly used "X-ray fluorescence analysis method" defined in JIS G1256 (1997), "spark discharge emission spectrophotometric analysis method" defined in JIS G1253 (2002) (hereinafter abbreviated as "emission spectrophotometric analysis method"), and "infrared absorption method after high-frequency induction heating combustion" defined in JIS G1215-4 (2010) (hereinafter abbreviated as "infrared absorption method).

However, these methods have a problem that time and accuracy of measurement are not sufficient when S concentration in hot metal is analyzed at a level of ppm. For example, "X-ray fluorescence analysis method" and "emission spectrophotometric analysis method" have a problem that a time of about 15 minutes is taken for providing an analyzed result of S concentration. Because, these methods require a smooth surface of about 30 mmϕ in diameter as an analytical surface since surface properties of the analytical surface such as surface roughness and the like exert on the analysis value, but it is not easy to cut and polish a hard sample of the pig iron and hence a pretreatment of the sample should be conducted precisely as disclosed in Patent Document 4. Also, a long time is taken when hot metal is taken and poured into a mold for an analyzing sample and cooled and then the resulting sample is taken out therefrom.

Further, "infrared absorption method" has a problem that scattering of S analysis value is caused in hot metal samples having a high carbon concentration. Because, when a steel sample is induction-heated at a high frequency, the temperature is instantly raised to about 1400° C. to start melting, and gaseous desulfurization progresses concurrently and is completed in a short time, whereas a hot metal sample of a low melting point is melted at about 1200° C., but decarburization is only caused at this stage and gaseous desulfurization starts in a delayed fashion and progresses slowly. When the pig iron sample is compared with the steel sample having the same S concentration, the generation of $SO_2$ by the gaseous desulfurization is slow and drowsy, so that when S concentration is low, signal/noise ratio becomes small and analysis accuracy becomes bad in the infrared absorption method having a large background. And also, the pig iron is hardly combusted as compared with steel, so that there is a problem that the measurement accuracy is poor because only a small amount of the sample is used for analysis.

As a method for solving the above measurement error in the infrared absorption method are developed a method wherein the measurement is repeated several times to take an average value, and a technique wherein a high accuracy is realized by continuously combusting the measuring sample several times, collecting into an adsorption/condensation column (trap) and analyzing a concentrated $SO_2$. However, these techniques require a long time in the analysis because the sample is measured or combusted several times, so that there is a problem that it is difficult to apply them to the analysis of S concentration in the hot metal. To this end, the X-ray fluorescence analysis method is frequently used in the analysis of S concentration in the hot metal.

PRIOR ART DOCUMENTS

Patent Documents

Patent Document 1: JP-A-2005-290434
Patent Document 2: JP-A-2009-191300
Patent Document 3: JP-A-2010-163697
Patent Document 4: JP-A-H08-094609

Non-Patent Documents

Non-patent Document 1: Tetsu-to-Hagane, vol. 58 (1972), p34
Non-patent Document 2: Sumitomo metal technical reports, vol. 45, No. 3 (1993), p52-58
Non-patent Document 3: Tetsu-to-Hagane, vol. 64 (No. 2) (1978), pA21-A24

SUMMARY OF THE INVENTION

Task to be Solved by the Invention

As mentioned above, the conventional method for analyzing S concentration in hot metal takes a long time in the analysis or has a problem in the analysis accuracy, which results in the increase of the fault of S concentration in the desulfurization treatment of the hot metal (decrease of on-target ratio), the increase of the amount of the desulfurization agent used, or the step disruption in subsequent steel making process.

The invention is made in view of the above problems of the conventional techniques and the object thereof is to propose a method for desulfurizing hot metal wherein S concentration in the hot metal is analyzed rapidly and precisely to rationalize the desulfurization treatment of the hot metal, whereby not only the fault of S concentration in the pretreatment of the hot metal but also the increase of the cost by excessive addition of the desulfurization agent and the step disruption in the steel-making step can be prevented.

Solution for Task

The inventors have made various studies on a method for rapidly and precisely analyzing S concentration in hot metal in order to solve the above task. As a result, it has been found that the task can be solved by combusting and oxidizing a hot metal sample taken at any stage before, during and after desulfurization treatment of the hot metal under high frequency induction heating in a pure oxygen atmosphere to convert all S included in the sample to $SO_2$ and analyzing a concentration of $SO_2$ through an ultraviolet fluorescence method, and the invention has been accomplished.

That is, the invention is a method for desulfurizing hot metal by analyzing S concentration of a sample taken out from the hot metal in at least one stage before, during and after desulfurization treatment of the hot metal, and conducting further subsequent desulfurization or judging an end of desulfurization or determining subsequent desulfurization conditions based on an analyzed value of S concentration, wherein the S concentration is analyzed by a method using an ultraviolet fluorescence method.

In the invention, it is preferable that the analyzing method of S concentration comprises a high frequency induction heating step of oxidizing the sample under a high frequency induction heating in a pure oxygen atmosphere to convert S in the hot metal to $SO_2$ and an analysis step of analyzing $SO_2$-containing gas generated in the high frequency induction heating step through an ultraviolet fluorescence method to quantify S concentration in the sample.

In the desulfurization treatment of the invention, it is preferable that a target S concentration is not more than 0.003 mass %.

Effect of the Invention

According to the invention, the S concentration of the hot metal can be analyzed and grasped rapidly and precisely, so that not only the desulfurization treatment can be rationalized to improve on-target ratio of S concentration but also excessive addition of the desulfurization agent can be suppressed and the step disruption in the steel making process can be prevented, and hence the industrially developing effect is large.

EMBODIMENTS FOR CARRYING OUT THE INVENTION

The inventors have considered that in order to prevent fault of S concentration in the desulfurization treatment as a pretreatment of hot metal, it is important to accurately analyze and grasp S concentration in the hot metal in at least one stage before, during and after the desulfurization treatment and reflect the analyzed result to judgment of continuing or ending desulfurization or desulfurizing conditions and made various studies on a method for analyzing S concentration in hot metal rapidly and in a high accuracy. As a result, S analyzing method using the following ultraviolet fluorescence method has been developed.

Figure 1:
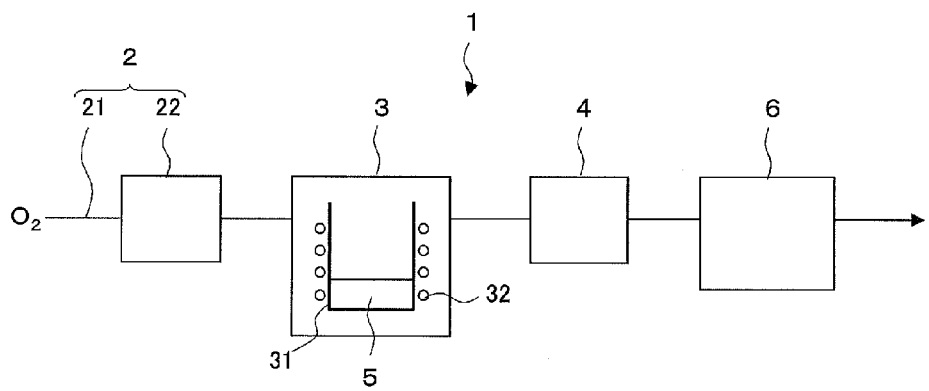
FIG. 1 is a schematic view illustrating a constructive example of S analyzing apparatus used in the invention.

FIG. 1 shows a constructive example of an analyzing apparatus using the ultraviolet fluorescence method. The ultraviolet fluorescence analyzing apparatus 1 comprises a pure oxygen supply means 2, a high frequency induction heating furnace 3 for combusting and oxidizing a pig iron sample 5 taken out from hot metal (hereinafter referred to as a sample simply) in a pure oxygen atmosphere supplied from the pure oxygen supply means 2 to convert S included in the sample 5 to $SO_2$, a dust filter 4 for removing grit and dust (dust) from $SO_2$-containing gas generated by combustion of the sample 5, and an ultraviolet fluorescence analyzing apparatus 6 for analyzing the $SO_2$-containing gas after the removal of the dust through ultraviolet fluorescence method to quantitatively analyze S in the sample.

The pure oxygen supply means 2 comprises a pure oxygen supply source having an oxygen concentration of not less than 99.5 vol % (not shown), a pure oxygen supply line 21, and a flow controller 22 disposed on the pure oxygen supply line 21 as a flow rate controlling means. As the flow controller 22 may be used a well-known flow controller, but it is preferable to use a mass flow controller capable of regulating a mass flow rate of pure oxygen from a viewpoint of controlling a flow rate of a gas supplied.

In the inside of the high frequency induction heating furnace 3 are arranged a ceramic crucible 31 for dissolving and combusting the sample 5 and a coil 32 surrounding the ceramic crucible 31, while an alternating current source (not shown) is connected to the coil 32. In the high frequency induction heating furnace 3, an alternating current of, for example, 10~20 MHz is applied to the coil 32 under a pure oxygen atmosphere supplied from the pure oxygen supply means 2, whereby the sample 5 in the ceramic crucible 31 is heated and dissolved rapidly, while S included in the sample 5 is reacted with oxygen or oxidized (combusted) to generate $SO_2$ (gas). Moreover, it is preferable to use a combustion improver such as tin, tungsten or the like in the combustion of the sample 5. Since the sample 5 can be heated and combusted rapidly by charging the sample 5 and the combustion improver into the ceramic crucible 31, the analysis of S concentration can be conducted promptly.

The dust filter 4 is disposed between the high frequency induction heating furnace 3 and the ultraviolet fluorescence analyzer 6 and removes dusts, which are generated from the sample 5 or the combustion improver, from $SO_2$-containing gas produced in the high frequency induction heating furnace 3 to protect ultraviolet fluorescence analyzer 6 arranged in subsequent stage. As the dust filter 4, it is preferable to use a material not adsorbing $SO_2$ and being excellent in the air permeability such as silica fiber or polytetrafluoroethylene.

In the ultraviolet fluorescence analyzer 6, an ultraviolet ray having, for example, a wavelength of 220 nm is irradiated to $SO_2$-containing gas, and fluorescence (wavelength: 330 nm) emitted in the returning of $SO_2$ from an excited state to a ground state is measured for a certain time, and then S amount included in the sample 5 is calculated from an integration value of fluorescence intensity measured with a previously prepared calibration curve. As the ultraviolet fluorescence analyzer 6 can be used a well-known ultraviolet fluorescence analyzer, concretely an ultraviolet fluorescence analyzer comprising an ultraviolet generating source, a fluorescence cell for irradiating ultraviolet ray to $SO_2$-containing gas, and a photomultiplier tube (PMT) measuring an excited light.

There will be described a method for quantitatively analyzing S concentration included in the sample 5 taken out from hot metal with the ultraviolet fluorescence analyzing apparatus 1 below.

At first, the sample 5 and the combustion improver are charged into the ceramic crucible 31. Then, pure oxygen is continuously supplied from the pure oxygen supply means 2 to the high frequency induction heating furnace 3, while an alternating current is applied to the coil 32 to combust (oxidize) the sample 5 in the pure oxygen atmosphere. After dusts included in $SO_2$-containing gas produced by the combustion of the sample 5 is removed by the dust filter 4, $SO_2$ amount in $SO_2$-containing gas is measured by the ultraviolet fluorescence analyzer 6 to quantify S concentration included in the sample 5.

According to the ultraviolet fluorescence analyzing apparatus 1, the sample 5 can be combusted rapidly and sufficiently with the high frequency induction heating furnace 3 in the pure oxygen atmosphere. In the ultraviolet fluorescence analyzing apparatus 1, $SO_2$ amount produced by the combustion of the sample 5 is measured by the ultraviolet fluorescence analyzer 6, so that the measurement is not substantially affected by humidity included in the gas to be measured or the temperature of the gas to be measured as compared to the conventional infrared absorption method measuring the infrared detector. Therefore, quantitative analysis of S can be conducted rapidly and accurately with a simple apparatus without requiring the arrangement of dehumidifier, adsorption/condensation column of $SO_2$ (trap) or the like. In the ultraviolet fluorescence analyzing apparatus 1, it is not necessary to use a reference gas (comparison gas) during the measurement as in the conventional technique. Since pig iron is hardly combusted as compared with steel, the measuring accuracy lowers in the infrared absorption method because only a small amount is analyzed, whereas the measurement can be conducted even at the small amount in the ultraviolet fluorescence method because the accuracy is high.

Further, oxygen absorbs fluorescence in the returning of $SO_2$ from the excited state to the ground state, or comes into collision with $SO_2$ molecule of the excited state to cause quenching (extinction) phenomenon. In the ultraviolet fluorescence method, therefore, it is known to decrease the measuring accuracy of $SO_2$ concentration when $SO_2$ amount in the gas to be measured is low or when a great amount of oxygen is included in the gas to be measured. In the ultraviolet fluorescence analyzing apparatus 1 of the invention, however, all S in the sample 5 can be oxidized in a short time with the high frequency induction heating furnace 3 combusting the sample in the pure oxygen. As a result, $SO_2$ concentration in the gas to be measured becomes high and fluorescence intensity measured by the ultraviolet fluorescence analyzer 6 indicates a lancet sharp peak, so that $SO_2$ amount can be measured accurately.

Moreover, oxygen has an action of quenching fluorescence of $SO_2$ as mentioned above, so that different fluorescence intensity is detected in response to oxygen concentration included in the gas to be measured ($SO_2$-containing gas) in the ultraviolet fluorescence method even if gas having the same $SO_2$ concentration is measured. Also, when the sample taken from hot metal is combusted, oxygen bonds to hydrogen, carbon or the like other than S included in the sample, so that non-oxygen gas other than $SO_2$ gas is generated.

In the ultraviolet fluorescence analyzing apparatus used in the invention, therefore, it is preferable to supply pure oxygen so that a difference between oxygen concentration in pure oxygen supplied to the high frequency induction heating furnace and oxygen concentration in $SO_2$-containing gas produced by the combustion of the sample is not more than 10 vol %, concretely oxygen concentration in $SO_2$-containing gas produced by the combustion of the sample is not less than 90 vol % in order to mitigate the aforementioned bad influence of oxygen. Because, when the sample is combusted, oxygen concentration in $SO_2$-containing gas is decreased by the formation of non-oxygen gas as compared with pure oxygen supplied to the high frequency induction heating furnace, but if oxygen concentration in $SO_2$-containing gas after the combustion is made to not less than 90 vol %, the change of fluorescence intensity by variation of oxygen concentration becomes small, and $SO_2$ amount can be measured accurately.

In order that a time of getting $SO_2$-containing gas produced in the high frequency induction heating furnace 3 into the ultraviolet fluorescence analyzer 6 is made short to shorten a time required for the analysis and further the resulting $SO_2$ is prevented from retaining in the apparatus, it is desirable that a flow rate of pure oxygen is ensured to be not less than a predetermined amount. However, if the flow rate of pure oxygen is made too large, $SO_2$ concentration in $SO_2$-containing gas decreases to deteriorate the measuring accuracy or frequency of clogging the dust filter 4 with dusts increases, so that the flow rate of pure oxygen is preferable to be adjusted properly depending on the size of the analyzing apparatus.

In the ultraviolet fluorescence method, the sample to be measured is combusted by high frequency induction heating in the pure oxygen atmosphere for a short time as mentioned above, so that S included in the sample can be oxidized to $SO_2$ rapidly and sufficiently. Also, $SO_2$-containing gas produced by the combustion of the sample is analyzed by the ultraviolet fluorescence method substantially free of background, so that S included in the sample can be analyzed by the ultraviolet fluorescence method in a high accuracy.

Now, when the S analysis method of the invention is applied to the analysis of the sample taken out from hot metal in at least one stage before, during and after the desulfurization treatment of the hot metal, S concentration in the hot metal can be measured rapidly and in a high accuracy, so that the end of the desulfurization or the further desulfurization is judged in the accurate grasping of S concentration in the hot metal. Alternatively, it is possible to determine subsequent desulfurization conditions, and hence it is possible to precisely control S concentration in the hot metal after the desulfurization treatment. Furthermore, new desulfurization efficiency can be accurately calculated by accurately grasping S concentration after the desulfurization treatment, so that there is an effect that desulfurization in subsequent charges can be conducted efficiently.

Moreover, a way of taking pig iron sample from the hot metal subjected to the measurement by the ultraviolet fluorescence method is not particularly limited, but a method defined, for example, in JIS G0417, appendix 3 can be used. In the latter method, an analysis sample can be obtained very simply by casting hot metal taken with a spoon or the like onto a clean iron plate to solidify into droplets and then pulverizing them to a size of about 1~2 mm with a hammer or the like.

In the invention, the preparation of the sample is easy and the measurement can be conducted rapidly, so that analytical values can be obtained within 3 minutes after the sampling of hot metal.

Example 1

Figure 2:
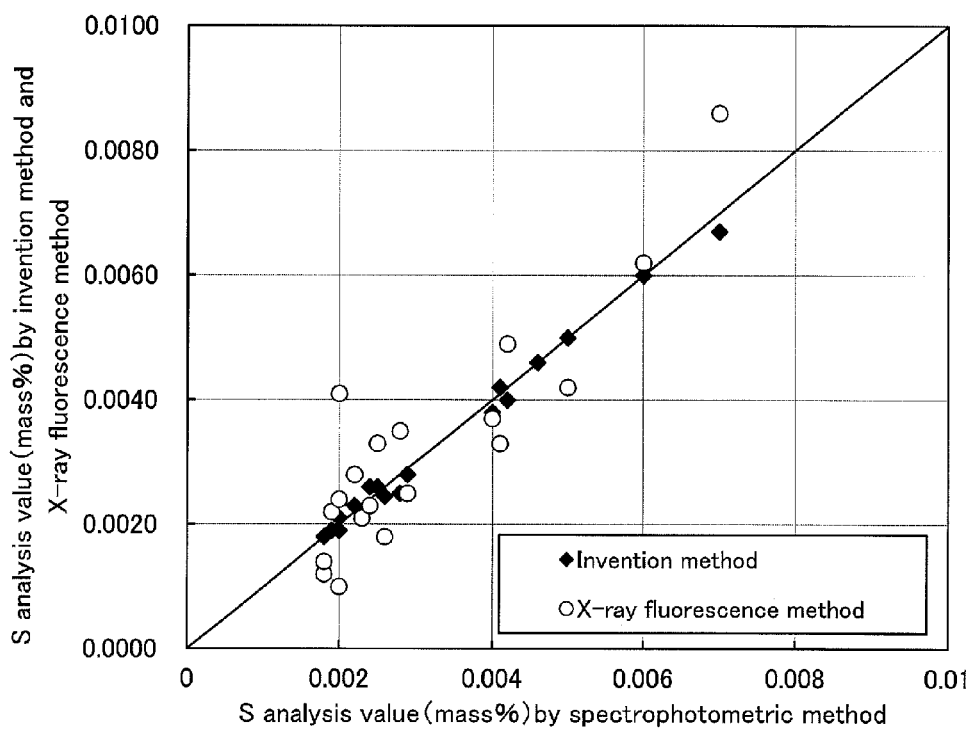
FIG. 2 is a graph showing a comparison of results when S concentration in hot metal is analyzed by using a methylene blue spectrophotometric method after separation of hydrosulfide, an X-ray fluorescence method and an ultraviolet fluorescence method of the invention.

FIG. 2 shows a comparison of results analyzed on S concentration when samples with different S concentrations taken from hot metal after desulfurization treatment with KR are analyzed by using a "methylene blue spectrophotometric method after separation of hydrosulfide" defined in JIS G1215-3 (2010) (hereinafter abbreviated as "spectrophotometric method"), an "X-ray fluorescence method" defined in JIS G1256 (1997) and an ultraviolet fluorescence method of the invention. The spectrophotometric method usually takes about several hours for analysis, but is a wet analysis method with a high accuracy. In a horizontal axis of FIG. 2 are shown S analysis values obtained by the spectrophotometric method as a standard, while S analysis values obtained by the X-ray fluorescence method and the ultraviolet fluorescence method of the invention are shown in a vertical axis thereof in comparison. As seen from FIG. 2, the S analysis values obtained by the ultraviolet fluorescence method of the invention are very coincident with the S analysis values obtained by the spectrophotometric method, while almost of the S analysis values obtained by the X-ray fluorescence method are largely divergent from the S analysis values obtained by the spectrophotometric method and hence the accuracy is poor.

This means that the end of the desulfurization can be judged precisely because S concentration can be measured by the ultraviolet fluorescence method of the invention in a higher accuracy than that of the conventional X-ray fluorescence method even in the measurement after the pretreatment of hot metal.

Example 2

Invention Example 1

After hot metal tapped from a blast furnace and having S concentration of 0.030~0.032 mass % is accommodated in a hot metal ladle, desulfurization of hot metal is carried out so as to reduce S concentration to not more than 0.002 mass % (acceptance: not more than 0.0024 mass %) with a commonly-used mechanical agitation type desulfurization apparatus (KR). Moreover, the S concentration after the tapping is a value measured by the X-ray fluorescence method defined in JIS G1256 (1997), and the desulfurization is carried out by charging a desulfurization agent composed mainly of CaO onto a hot metal surface in the hot metal ladle in an amount of 10 kg per 1 ton of hot metal and rotating an impeller of KR in the hot metal for a given time. After the lapse of the given time, the rotation of the impeller is stopped and S concentration in the hot metal is determined by analyzing a sample take from the hot metal with the ultraviolet fluorescence method of the invention. Then, a proper amount of the desulfurization agent is additionally added so that S concentration after the desulfurization is 0.0020 mass % based on the S analysis value, and thereafter the impeller is again rotated in the hot metal for 2 minutes to end the desulfurization.

Invention Example 2

After hot metal tapped from the blast furnace and having S concentration of 0.030~0.032 mass % is accommodated in a hot metal ladle likewise Invention Example 1, desulfurization of hot metal is carried out so as to reduce S concentration to not more than 0.002 mass % (acceptance: not more than 0.0024 mass %) with the same KR as in Invention Example 1. Moreover, S concentration after the tapping is a value analyzed by the ultraviolet fluorescence method of the invention, and the desulfurization is conducted by charging the desulfurization agent composed mainly of CaO onto a hot metal surface in the hot metal ladle and rotating the impeller of KR in the hot metal for a given time and the rotation of the impeller is topped to end the desulfurization. And also, the desulfurization agent is charged so that S concentration after the desulfurization is 0.0020 mass % based on the S value analyzed by the ultraviolet fluorescence method.

Comparative Example

After hot metal tapped from the blast furnace and having S concentration of 0.030~0.032 mass % is accommodated in a hot metal ladle likewise Invention Example 1, desulfurization of hot metal is carried out so as to reduce S concentration to not more than 0.002 mass % (acceptance: not more than 0.0024 mass %) with the same KR as in Invention Example 1. Moreover, S concentration after the tapping is a value measured by the X-ray fluorescence method defined in JIS G1256 (1997), and the desulfurization is conducted by charging the desulfurization agent composed mainly of CaO onto a hot metal surface in the hot metal ladle and rotating the impeller of KR in the hot metal for a given time and the rotation of the impeller is stopped to end the desulfurization. And also, the desulfurization agent is charged so that S concentration after the desulfurization is 0.0020 mass % based on the S value analyzed by the X-ray fluorescence method.

In each of Invention Example 1, Invention Example 2 and Comparative Example, a sample is taken out from the hot metal ladle after the end of the desulfurization to analyze S concentration in the sample by the spectrophotometric method defined in JIS G1215-3. Under the conditions of Invention Example 1, Invention Example 2 and Comparative Example, the desulfurization is conducted for 35 charges in Invention Example 1, 33 charges in Invention Example 2 and 41 charges in Comparative Example, respectively, and then S concentration in the sample is analyzed to determine a fault ratio to acceptance/rejection criterion (not more than 24 massppm) (charge number of S fault/total charge number× 100(%)), and results thereof are shown in Table 1.

TABLE 1

| | Analysis stage and analysis method of S concentration | | | |
|---|---|---|---|---|
| | before desulfurization | during desulfurization | after desulfurization | Ratio of S fault (%) |
| Invention Example 1 | X-ray fluorescence method | Invention method | spectrophotometric method | 0.0 |
| Invention Example 2 | Invention method | — | spectrophotometric method | 3.0 |
| Comparative Example | X-ray fluorescence method | — | spectrophotometric method | 9.8 |

As seen from Table 1, the fault of S concentration after the desulfurization of the hot metal can be largely reduced by analyzing S concentration in the hot metal by the ultraviolet fluorescence method of the invention in at least one stage before and during the desulfurization as the pretreatment of hot metal and reflecting the analyzed results to subsequent desulfurization.

Example 3

Invention Example

After hot metal tapped from the blast furnace and having S concentration of 0.030~0.032 mass % is accommodated in a hot metal ladle likewise Invention Example 1 of Example 2, desulfurization of hot metal is conducted so as to reduce S concentration to not more than 0.002 mass % (acceptance: not more than 0.0024 mass %) with the same KR as in Invention Example 1 of Example 2. Hot metal having an analysis value of 22~24 massppm by analyzing pig iron after the desulfurization with the ultraviolet fluorescence method of the invention is subjected to decarburization refining in a converter to obtain molten steel of about 300 tons, and then the molten steel is tapped into a ladle to rapidly analyze S concentration of molten steel in the ladle by the ultraviolet fluorescence method.

Comparative Example

After hot metal tapped from the blast furnace and having S concentration of 0.030~0.032 mass % is accommodated in a hot metal ladle likewise Invention Example 1 of Example 2, desulfurization of hot metal is conducted so as to reduce S concentration to not more than 0.002 mass % (acceptance: not more than 0.0024 mass %) with the same KR as in Invention Example 1 of Example 2. Hot metal having an analysis value of 22~24 massppm by analyzing pig iron after the desulfurization with the X-ray fluorescence method is subjected to decarburization refining in a converter to obtain molten steel of about 300 tons, and then the molten steel is tapped into a ladle to rapidly analyze S concentration of molten steel in the ladle by the ultraviolet fluorescence method.

The desulfurization of hot metal in the above Invention Example and Comparative Example is conducted for 20 charges, respectively, and S analysis result of the resulting molten steel after the tapping is checked with acceptance/rejection criterion (not more than 34 massppm) to determine a fault ratio (charge number of S fault/total charge number× 100(%)). As a result, all charges are acceptance in Invention Example, while 3 charges are rejection in Comparative Example. To this end, additional desulfurization of such rejected charges is necessary to be conducted in secondary refining, and step disruption is caused.

From the above results, it has been confirmed that since the accurate analysis value is obtained by analyzing S concentration in hot metal after the desulfurization of the hot metal by the analysis method using the ultraviolet fluorescence method of the invention, accidental S fault in the tapping from the converter can be avoided by adding an expected value of S pickup in the refining in the converter to such an analysis value. Moreover, as S concentration of molten steel sample after the tapping is separately analyzed by the spectrophotometric method, the analyzed result is coincident with the result rapidly analyzed by the ultraviolet fluorescence method. Further, the amount of S pickup in decarburization refining in the converter is assessed to be about 7 massppm.

INDUSTRIAL APPLICABILITY

Although the above is explained with respect to the analysis of S concentration in hot metal during the desulfurization, the technique of the invention is not limited to such a field and can be applied to the measurement of S concentration in the other non-combustible metals and is applicable to refining of, for example, ferronickel.

DESCRIPTION OF REFERENCE SYMBOLS

1: ultraviolet fluorescence analyzing apparatus
2: pure oxygen supply means
21: pure oxygen supply line
22: flow controller
3: high frequency induction heating furnace
31: ceramic crucible
32: coil
4: dust filter
5: sample
6: ultraviolet fluorescence analyzer

The invention claimed is:

1. A method for desulfurizing molten hot metal, the method comprising:
   taking a sample out from the molten hot metal in at least one stage of before, during, and after a desulfurization treatment of the molten hot metal,
   analyzing an S concentration of the sample and determining an S concentration of the molten hot metal, and
   based on the determined S concentration, (i) conducting further subsequent desulfurization, (ii) judging an end of desulfurization, or (iii) determining subsequent desulfurization conditions,
   wherein the S concentration of the sample is analyzed by a method comprising:
      oxidizing the sample under high frequency induction heating in a pure oxygen atmosphere to convert S in the sample to $SO_2$ by supplying pure oxygen with an oxygen concentration of not less than 99.5 vol.%, the high frequency inducting heating step generating an $SO_2$-containing gas by combustion of the sample, and
      analyzing the $SO_2$-containing gas generated in the high frequency induction heating step through an ultraviolet fluorescence method to quantify S concentration in the sample.

2. The method for desulfurizing the molten hot metal according to claim 1, wherein a target S concentration in the desulfurization method is not more than 0.003 mass %.

3. The method for desulfurizing the molten hot metal according to claim 1, wherein a difference between oxygen concentration in the pure oxygen and in the $SO_2$-containing gas is not more than 10 vol.%.

4. The method for desulfurizing the molten hot metal according to claim 1, wherein the ultraviolet fluorescence method does not use a dehumidifier.

* * * * *